Aug. 23, 1938. R. W. FAIR Plant Pat. 283
PEACH TREE
Filed Dec. 2, 1937
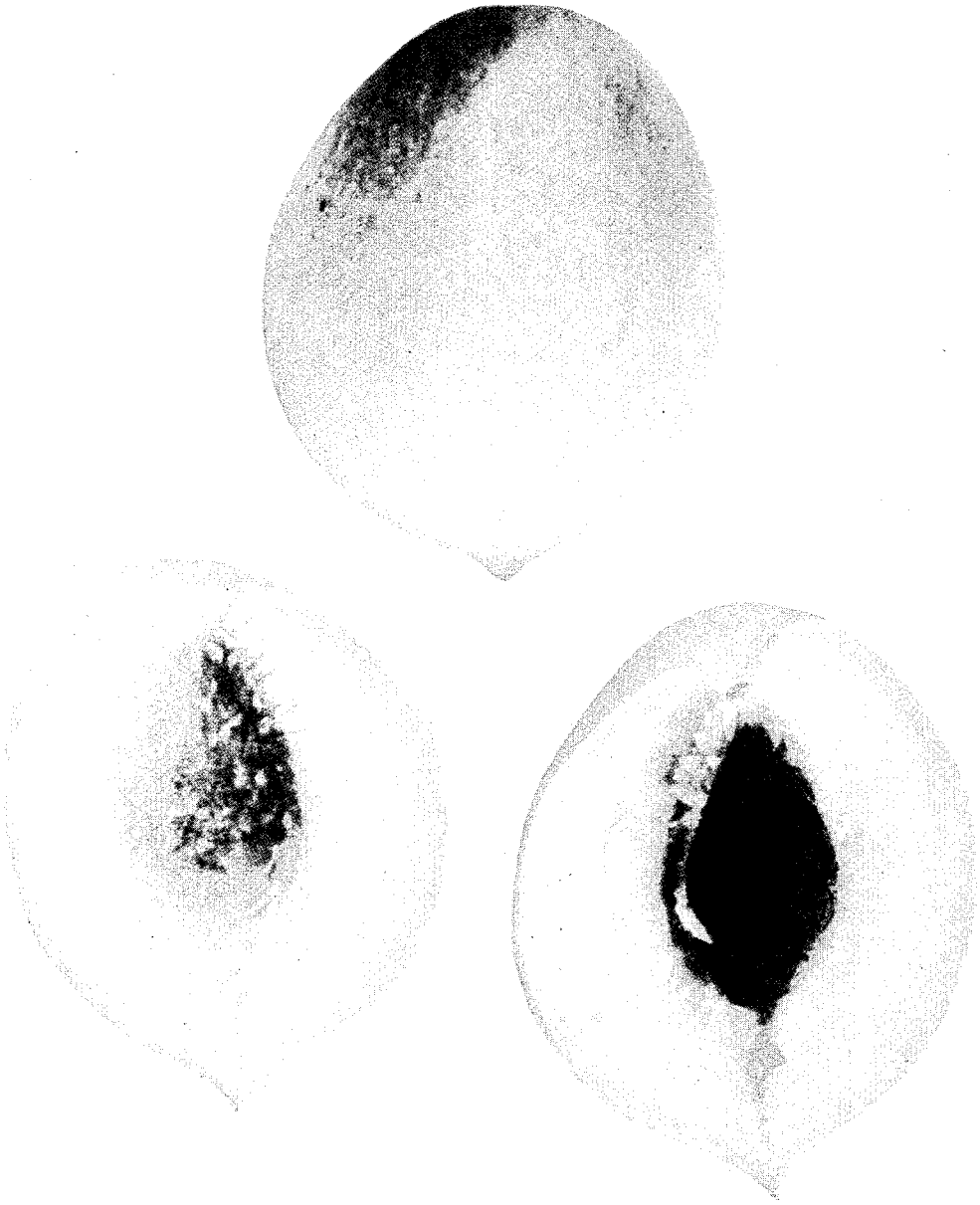
Inventor
R. W. Fair
By Robb & Robb
attorneys Patented Aug. 23, 1938

Plant Pat. 283

UNITED STATES PATENT OFFICE

283

PEACH TREE

Robert Walter Fair, Tyler, Tex.

Application December 2, 1937, Serial No. 177,812

1 Claim. (Cl. 47—62)

The new and distinct variety of peach tree herein referred to is the outcome of a definite search by me for a yellow free-stone peach ripening ahead of the well known Elberta.

It is generally recognized that there is always a good price and a good demand for the first Elbertas reaching the market and it was to obtain this advantage that I first planted and closely watched a group of seedlings from which I selected this as the most outstanding for development and propagation. The new variety was propagated by budding and is believed to be a cross between Fair Beauty, originated by me, and the Elberta.

The present variety possesses a number of desirable characteristics, the first and most important of which is the early ripening period. From comparative tests under comparable conditions I find my new variety begins to ripen fully a week to ten days ahead of the old established Elberta, thus affording from the commercial standpoint the advantages of procurement of the earliest Elberta prices for the whole of the crop from this variety.

An equally important distinction between this variety and the Elberta is found in the fruit in that it has a smoother and brighter color, causing it to show up better on the market, due mainly to the scantiness of pubescence. Its clean appearance makes it a more attractive peach.

Furthermore, it has a good flavor, better than that of the Elberta.

The original drawing annexed hereto shows a view of the whole peach and views of the halves of the peach, one of which includes the seed, all of actual size.

Asexual reproduction shows the variety comes true to form.

The following is a detail description of this new variety, all references to color being in accordance with Ridgway's Color Standard and Nomenclature, except where the ordinary dictionary definition is obviously meant:—

Tree:
- Medium size, medium strength;
- Spreading, vase formed;
- Hardy, productive, regular bearer.

Trunk:
- Medium size;
- Smooth.

Branches:
- Medium size, smooth;
- Color—brown, with greenish cast.

*Lenticels.*—Numerous, medium size.

Leaves:
- Length—5½ inches;
- Width—1 inch to 1⅜ inches;
- Medium size.
- Lanceolate, acutely pointed;
- Medium thickness;
- Smooth and undulate.
- Color—medium green.

*Margin.*—Glandular, finely serrate.

*Petiole.*—Medium length; medium thickness.

*Glands.*—Average number—43. Alternate, medium size, mixed shape. Color—green. Position—irregular.

Flower-buds:
- Hardy, medium size, medium length;
- Pointed, free.

Flowers:
- The variety blooms from March 15th to 20th in the vicinity of Swan, Texas, where specimens of the variety were grown. This is mid-season compared with other varieties. The flowers are medium in size and of a salmon color.

Fruit:
- Maturity when described—fully ripe.
- Date—July 15th.

*Size.*—Medium, uniform. Diameter—axial 4½ inches. Transverse in suture plane 3½ inches. At right angles to suture plane about 3¼ inches.

*Form.*—Uniform. Unsymmetrical, broadly oblong; compressed laterally toward suture.

*Suture.*—Distinct, extending from the base to the apex, and does not extend beyond the pistil point.

*Ventral surface.*—Slightly rounded.

*Cavity.*—Flaring and elongated in suture plane with suture showing at one side. Depth—⅝ inch. No marking.

*Base.*—Slightly oblique.

*Apex.*—Mammiform. Pistil point—apical.

*Stem.*—Length—⅜ inch. Medium size, medium strength. Adherence to stone—moderate.

*Skin.*—Medium thickness, medium tenderness. Free from the flesh when thoroughly ripe. Tendency to crack—slight, none in wet season. Color—Brazil red to Geranium pink, heavy blush over a light orange yellow base. Down—scant.

*Flesh.*—Color—yellow to light orange yellow from the skin in and stained with red near pit. Surface of pit cavity—red flecked with white. Juice—abundant, rich. Texture—medium fine, firm, melting. Fibres—few, fine, tender. Ripens—evenly. Flavor—subacid, mild. Aroma—pronounced. Eating quality—good.

*Stone.*—Free, retains short fibre like threads along ridges. Size—medium. Length—2½ inches; breadth—1¼ inches. Form—oblong, cuneate toward base. Base—straight and narrow. Apex—rounded. Sides—unequal, curved on right side. Surface—irregularly furrowed toward apex. Ridged near the base and pitted from base to above center. Ridges—jagged toward apex. Pits—elongated. Ventral edge—thick. Dorsal edge—narrow, with narrow to broad grooves toward base. Ridges on either side—interrupted.

Use:

Market, local, dessert, culinary, canning.

Keeping quality:

Good.

Resistance to insects and diseases:

Good.

Shipping quality:

Good.

General notes:

In all details the new peach closely resembles the Elberta tree in form and shape; also Fair's Beauty. It closely resembles the Elberta in time of bloom, and in flower and fruit, but has proven more hardy than either of the above named varieties in adjacent plantings, and is earlier than Elberta.

I claim:

A new and distinct variety of peach tree characterized by its similarity to the Elberta in general details, but having an earlier ripening period of its fruit, a smoother and brighter color of the fruit due to scantiness of pubescence, and better flavor, substantially as shown and described.

ROBERT WALTER FAIR.